United States Patent
Gerlach et al.

(10) Patent No.: US 12,318,461 B2
(45) Date of Patent: *Jun. 3, 2025

(54) SALICYLIC ACID GEL

(71) Applicant: Vantage Specialty Ingredients, Inc., Warren, NJ (US)

(72) Inventors: Chris D. Gerlach, Buford, GA (US); Michael B. Davies, Dacula, GA (US)

(73) Assignee: Vantage Specialty Ingredients, Inc., Warren, NJ (US)

( * ) Notice: Subject to any disclaimer, the term of this patent is extended or adjusted under 35 U.S.C. 154(b) by 480 days.

This patent is subject to a terminal disclaimer.

(21) Appl. No.: 17/373,070

(22) Filed: Jul. 12, 2021

(65) Prior Publication Data

US 2021/0338540 A1 Nov. 4, 2021

Related U.S. Application Data

(63) Continuation of application No. 15/880,764, filed on Jan. 26, 2018, now abandoned, which is a continuation of application No. 14/329,063, filed on Jul. 11, 2014, now abandoned, which is a continuation-in-part of application No. PCT/US2013/062561, filed on Sep. 30, 2013, which is a continuation-in-part of application No. 13/789,780, filed on Mar. 8, 2013, now Pat. No. 8,828,979.

(60) Provisional application No. 61/990,144, filed on May 8, 2014, provisional application No. 61/615,956, filed on Mar. 27, 2012.

(51) Int. Cl.

| | | |
|---|---|---|
| A61K 8/04 | (2006.01) |
| A61K 8/34 | (2006.01) |
| A61K 8/365 | (2006.01) |
| A61K 8/42 | (2006.01) |
| A61K 8/73 | (2006.01) |
| A61K 8/86 | (2006.01) |
| A61K 9/00 | (2006.01) |
| A61K 9/06 | (2006.01) |
| A61K 31/16 | (2006.01) |
| A61K 31/60 | (2006.01) |
| A61K 47/10 | (2017.01) |
| A61K 47/18 | (2017.01) |
| A61K 47/38 | (2006.01) |
| A61Q 5/00 | (2006.01) |
| A61Q 5/02 | (2006.01) |
| A61Q 19/00 | (2006.01) |
| A61Q 19/10 | (2006.01) |

(52) U.S. Cl.
CPC .............. *A61K 8/042* (2013.01); *A61K 8/342* (2013.01); *A61K 8/365* (2013.01); *A61K 8/42* (2013.01); *A61K 8/731* (2013.01); *A61K 8/86* (2013.01); *A61K 9/0014* (2013.01); *A61K 9/06* (2013.01); *A61K 31/16* (2013.01); *A61K 31/60* (2013.01); *A61K 47/10* (2013.01); *A61K 47/18* (2013.01); *A61K 47/38* (2013.01); *A61Q 5/006* (2013.01); *A61Q 5/02* (2013.01); *A61Q 19/00* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,505,949 | A * | 4/1996 | Benitez | A61K 31/621 514/859 |
| 6,455,058 | B1 * | 9/2002 | Sun | A61Q 5/006 424/70.21 |
| 2006/0239953 | A1 * | 10/2006 | Clapp | A61Q 1/14 424/70.22 |
| 2009/0214628 | A1 * | 8/2009 | de Rijk | A61Q 5/006 424/47 |
| 2012/0014885 | A1 * | 1/2012 | Collier | A61Q 15/00 424/59 |

\* cited by examiner

*Primary Examiner* — Patricia Duffy
*Assistant Examiner* — Garen Gotfredson
(74) *Attorney, Agent, or Firm* — Louis C. Paul

(57) ABSTRACT

A salicylic acid gel contains salicylic acid, a thickener, and a stabilizer compound. The gel may be diluted and/or incorporated into final skin care products.

12 Claims, No Drawings

SALICYLIC ACID GEL

CROSS-REFERENCE TO RELATED APPLICATIONS

This application is a continuation of U.S. application Ser. No. 15/880,764, filed Jan. 26, 2018, which application is a continuation of U.S. application Ser. No. 14/329,063, filed Jul. 11, 2014 (now abandoned), which application claims benefit of U.S. 61/990,144 filed May 8, 2014 and is a continuation in part of PCT/US13/62561 filed Sep. 30, 2013 which is a continuation in part of U.S. Ser. No. 13/789,780 filed Mar. 8, 2013 (now U.S. Pat. No. 8,828,979 issued Sep. 9, 2014), which claims benefit of U.S. 61/615,956 filed Mar. 27, 2012, each application hereby incorporated by reference in its entirety.

FIELD OF THE INVENTION

The invention relates to a stable gel of salicylic acid, and products produced therefrom.

BACKGROUND OF THE INVENTION

Salicylic acid, also known as 2-hydroxybenzenecarboxylic acid, is a monohydroxybenzoic acid. Its salts and esters are known as salicylates. Salicylic acid has the formula:

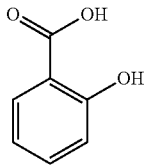

Salicylic acid is also known for providing pain relief when applied as a liniment, for example Salicylic acid is used in many skin-care products. For example, salicylic acid is well known for its use in anti-acne treatments. In addition to the treatment of acne, salicylic acid is also used in products for treatment of psoriasis, calluses, corns, skin tags, keratosis pilaris, and warts. It works as a keratolytic, bacteriocide and comedolytic agent. Salicylic acid is also used in shampoos for treatment of dandruff and as a chemical exfoliant.

Salicylic acid can cause burns if applied in high concentrations. Typically, over-the-counter limits are 2% for topical treatments (that remain on the skin) and 3% for cleansers or shampoo (products that are washed off) Higher concentrations (e.g. up to 40 wt %) may be used for wart and skin tag removal but should be applied cautiously and only to the wart and not the surrounding skin.

Salicylic acid is poorly soluble in water. It is therefore difficult to prepare solutions of salicylic acid that remain precipitate-free.

BRIEF SUMMARY OF THE INVENTION

The present invention is directed to a stable salicylic acid gel consisting of salicylic acid, a thickener, and a stabilizer compound, wherein the salicylic acid is present in at least 1 wt % based on total weight of the gel. The present invention is further directed to a salicylic acid solution comprising the salicylic acid gel, a thickener, and a solvent. The present invention is further directed to products prepared with the salicylic acid gel or with dilute solutions of the gel.

The present invention is further directed to a stable salicylic acid gel comprising salicylic acid, a thickener, and a stabilizer compound, wherein the salicylic acid comprises at least 30 wt %, based on total weight of the gel. The present invention is further directed to a salicylic acid solution comprising the salicylic acid gel and a solvent. The present invention is further directed to products prepared with the salicylic acid gel or with dilute solutions of the gel in solvent. The present invention is further directed to a salicylic acid gel consisting of salicylic acid, a thickener, and a stabilizer compound, wherein the salicylic acid comprises at least 30 wt %, based on total weight of the gel.

In further aspects, the salicylic acid gel prepared in accordance with any aspect above is combined with ingredients to form various products including body or hand lotions, skin exfoliation products, skin tag removers, anti-dandruff shampoos, wart medications, and anti-acne medications.

Further aspects are directed to making a solution or skin care product comprising mixing the salicylic acid gel in accordance with any aspect defined above with a solvent.

DETAILED DESCRIPTION OF THE INVENTION

Aspects of the invention are directed to a gel of salicylic acid, at least one thickener, and at least one stabilizer compound selected from nitrogen compounds. One aspect is particularly directed to a stable, concentrated gel. The concentrated gel allows relatively large amounts of salicylic acid to be shipped and stored in a safe and stable manner. A higher concentration of salicylic acid further allows smaller shipping and storage space. Another aspect is directed to gel consisting of salicylic acid, at least one thickener, and at least one stabilizer compound selected from nitrogen compounds. This gel also allows salicylic acid to be shipped and stored in a safe and stable manner.

The thickener increases the viscosity of the gel. The thickened gel allows for use in formulas with higher final viscosity such as wart, callus, and skin tag removers. These materials often use higher levels of salicylic acid. Since the gel is thickened it allows for a thicker final product or less viscosity adjustments for the manufacturer than if the thinner gel was used.

In one aspect, a (concentrated) salicylic acid gel comprises at least 30 wt % salicylic acid, at least 35 wt %, or at least 40 wt % salicylic acid gel, for example 30 wt % to 60 wt % salicylic acid, or 35 wt % to 55 wt %, or 40 to 55 wt % salicylic acid each based on total weight of the gel. Specific amounts may be 30 wt %, 35 wt %, 40 wt %, 50 wt %, and 60 wt % based on total weight of the gel based on total weight of the gel.

The concentrated salicylic acid gel comprises the stabilizer compound in an amount of at least 40 wt %, at least 45 wt %, at least 60 wt %, and up to 70 wt %, for example 40 to 70 wt %, or 45 to 60 wt %, each based on total weight of the gel which is an amount effective to provide stability to the salicylic acid in the gel. Specific amounts may be 40 wt %, 50 wt %, 60 wt %, 65 wt %, and 70 wt % based on total weight of the gel. The concentrated salicylic acid gel comprises the thickener compound in an amount of at least 1 wt %, at least 5 wt %, at least 10 wt %, at least 20 wt %, at least 30 wt % and up to 50 wt %, for example 1 to 20 wt %, or 5 to 15 wt %, each based on total weight of the gel which is amount effective to provide thickening of the salicylic acid gel. Specific amounts may be 1 wt %, 5 wt %, 10 wt %, 15 wt % and 20 wt % based on the total weight of the gel.

The ratio of the thickener to salicylic acid and stabilizer compound depends on the thickener being used. For example, if cellulose is being used the ratio can be relatively high (47:1) whereas if a wax is used like stearyl alcohol or PEG-450 the ratio will be lower (4:1). The amount of thickener may also depend on the ultimate product. For example, if the ultimate product is a stick, such as an acne stick, the amount of thickener may be higher than the amount needed to produce, for example, an acne lotion. For example, stearyl alcohol at 10% provides a material with a viscosity greater 100,000 cps, at 20% provides essentially a soft solid or extremely thick gel. Hydroxypropylcellulose (HPC) at 3% gives a syrupy gel with a viscosity greater than 100,000 cps.

In one aspect, the concentrated salicylic acid gel is formed by mixing salicylic acid with the stabilizer compound until the salicylic acid is dissolved in the stabilizer compound. The thickener is than added to increase the viscosity of the gel.

In a particular aspect, no water or solvent such as ethanol is included in the gel. In a further particular aspect, no other active ingredient is present in the gel. In a particular aspect, there are only three components that form the concentrated gel: the stabilizer compound (complexing agent), the thickener, and the salicylic acid. That is the salicylic acid gel consists of salicylic acid, a thickener, and a stabilizer compound, wherein the salicylic acid comprises at least 30 wt %, based on total weight of the gel.

The mixing of the salicylic acid, the thickener, and the stabilizer compound may be done at room temperature. Alternatively the mixing may occur at an elevated temperature such as up to 80° C. After initial heating and blending, the temperature may be gradually reduced with continued mixing until room temperatures are reached (20-25° C.). Generally mixing takes about 30 to 180 minutes.

The concentrated gel may then be stored for future use. A benefit of the concentrated gel is that such gel contains very concentrated amounts of salicylic acid, and less storage space is required than dilute solutions of salicylic acid. The gel is storage stable for at least 2 years.

The thickener may be any suitable nonionic thickener that increases the viscosity of the salicylic acid gel. The resulting material can have viscosities from a flowable liquid to a solid bar or stick. For those materials where it is possible and reasonable to measure the viscosity, a Brookfield viscometer with a heliopath can be used. Typically these measurements are made at room temperature (20° C.-25° C.). Nonionic thickeners useful to increasing the viscosity of the concentrated salicylic acid gel include, but are not limited to, agar, align, pectin, bentonite, chitosan, cellulose, carrageenan, chitin, cassia gum, cetyl glycol, clay, croscarmellose, dextrin, xanthan gum, gelatin, hectorite, silica, hydroxyethylcellulose, hydroxypropylcellulose, methylcellulose, microcrystalline cellulose, pectin, polyester-5, polyether-1, polyglycerin-20, polyglycerin-40, sclerotium gum, sodium stearate, stearyl alcohol, starch, beeswax and ceresin.

The thickener may also be an alcohol such as an alcohol containing at least 9 carbon atoms, for example, 9-11, 12-13, 12-15, 20-22, 30-50, and 40-60 carbon atoms. Specific alcohols include cetearyl alcohol, cetyl alcohol, decyl alcohol, lauryl alcohol, and polyvinyl alcohol.

The thickener may also be a polyethylene glycol such as PEG-450, PEG-800, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, and PEG-180M.

Mixtures of any of the thickeners may also be used. Particular thickeners useful in the present invention are PEG-450, stearyl alcohol, and hydroxypropyl cellulose.

The stabilizer compound may be any suitable nitrogen compound that stabilizes the salicylic acid in the concentrated gel. Nitrogen compounds useful to form the highly concentrated salicylic gel include, but not limited to, alkoxylated amides, alkoxylated amines, alkylamido alkylamines, amides, amine oxides, and amines. Ideally, a clear product should be produced.

In one aspect, the nitrogen compound is cocamidopropyl dimethylamine. The cocamidopropyl dimethylamine is particularly suitable for high concentrations of salicylic acid. When diluted in water, the resulting solution is stable and clear.

The concentrated gel can be diluted to any suitable level for use. Dilution of the salicylic acid gel may occur by the addition of water. Upon dilution, the salicylic acid forms a clear, stable solution in the water—that is, the salicylic acid does not precipitate out.

In particular the dilute solutions comprise wherein the concentration of the salicylic acid in the solution is at least 0.5 wt %, at least 1 wt %, at least 5 wt %, at least 10 wt %, at least 15 wt % or at least 20 wt % each based on total weight of the solution.

The present invention is further directed to products prepared with the salicylic acid gel or with dilute solutions of the gel in solvent wherein the concentration of the salicylic acid in the product is at least at least 0.5 wt %, at least 1 wt %, at least 5 wt %, at least 10 wt %, at least 15 wt %, at least 20 wt %, at least 30 wt %, or at least 40 wt % each based on total weight of the product.

Other aspects of the invention are directed to a gel consisting of salicylic acid, at least one thickener, and at least one stabilizer compound selected from nitrogen compounds. The gel allows salicylic acid to be shipped and stored in a safe and stable manner.

The salicylic acid gel consists of at least 1 wt %, at least 5 wt %, at least 10 wt %, at least 15 wt %, or at least 20 wt %, salicylic acid based on total weight of the gel. Specific amounts may be, but not limited to, 1 wt %, 5 wt % 10 wt %, or 20 wt %.

The salicylic acid gel consists of the stabilizer compound in an amount of at least 30 wt %, at least 80 wt %, at least 90 wt %, at least 95 wt %, at least 99 wt %, and up to 99 wt %, for example between 70 wt % and 99 wt %.

The salicylic acid gel consists of the thickener in an amount of at least 1 wt %, at least 5 wt %, at least 10 wt %, at least 20 wt %, at least 30 wt % and up to 50 wt %, for example between 20 wt % and 50 wt %.

In one aspect, the salicylic acid gel is formed by mixing salicylic acid with the stabilizer compound and thickener until the salicylic acid is dissolved in the stabilizer compound. No water or solvent such as ethanol is included in the gel.

The mixing of the salicylic acid and the stabilizer compound may be done at room temperature. Alternatively the mixing may occur at an elevated temperature such as up to 80° C. After initial heating and blending, the temperature may be gradually reduced with continued mixing until room temperatures are reached (20-25° C.). Generally mixing takes about 3 to 180 minutes. The gel is stable and may be stored.

The stabilizer compound may be any suitable nitrogen compound that stabilizes the salicylic acid in the gel as discussed above and incorporated by reference herein.

The thickener may by any suitable nonionic thickener that increase the viscosity of the salicylic acid gel as discussed above and incorporated by reference herein. It was discovered that a thickener may be added to the salicylic acid and stabilizing agent without affecting the stability of the gel.

As discussed above, the gel can be diluted to any suitable level for use such as by the addition of water. In particular the dilute solutions comprise wherein the concentration of the salicylic acid in the solution is at least 0.5 wt %, at least 1 wt %, at least 5 wt %, at least 10 wt %, at least 15 wt % or at least 20 wt % each based on total weight of the solution. Upon dilution, the salicylic acid forms a clear, stable solution in the water.

The present invention is further directed to products prepared with the salicylic acid gel or with dilute solutions of the gel in solvent wherein the concentration of the salicylic acid in the product is at least at least 0.5 wt %, at least 1 wt %, at least 5 wt %, at least 10 wt %, at least 15 wt % or at least 20 wt % each based on total weight of the product.

For pH evaluation, 94.5 wt % water was added to 5.5 wt % of the concentrated gel (36 wt % salicylic acid, 10 wt % PEG-450, 54 wt % cocamidopropyl dimethylamine) resulting in a 2 wt % salicylic acid concentration; the maximum allowed for anti-acne products. The same evaluation was run using 91.7 wt % water and 8.3 wt % of the gel (resulting in 3 wt % active salicylic acid; the maximum allowed for anti-dandruff products) and 33.3 wt % water and 66.7 wt % of the gel (resulting in 24 wt % active salicylic acid) to evaluate for the wart remover monograph. All of these studies resulted in clear, stable solutions with pH levels between 3 and 4.5.

The pH of the dilute system is generally less than 5, such as 2 to 5, 2.5 to 4.5, typically 3 to 4.

For topical purposes, the dilute system must pass the USP Monograph for a Salicylic Gel which includes an assay for salicylic acid.

The diluted product may be combined with other suitable ingredients to form the final products such as creams, lotions, make-ups, toners, astringents, skin cleansing compositions, shampoos, skin tag removers, exfoliants, and conditioners. These compositions contain about 0.1-40 wt % of salicylic acid. The amount of salicylic acid in the final product depends on the intended purpose of the product.

Creams typically contain about 10-90 wt % water and 10-90 wt % oil. Creams may also contain humectants, emollients, surfactants, emulsifiers, preservatives and fragrances. Creams would generally contain from 0.1 to 10 wt % salicylic acid.

Lotions typically contain 20-80 wt % oil and 10-80 wt % water in an emulsion form. In addition, lotions may contain humectants, emollients, surfactants, fragrances, preservatives and so forth. Creams would generally contain from 0.2 to 10 wt % salicylic acid.

Make-ups typically contain about 5-70 wt % oil, 10-95 wt % water, and about 5-40 wt % pigment. In addition, the makeup may contain surfactants, silicones as part of the oil phase, humectants, emollients, preservatives, fragrances, etc. Make-up would generally contain from 0.1 to 3 wt % salicylic acid.

Anti-dandruff shampoos typically contain 1-40 wt % of a cleansing surfactant and 10-90 wt % water. The shampoo may also contain any one of ingredients such as surfactants, colorants, preservatives, fragrance, emulsifiers, viscosity adjusters, and conditioning agents. Anti-dandruff shampoos would generally contain from 0.18 to 3 wt % salicylic acid.

Hair conditioners typically contain include 10-95 wt % water, 0.5-30 wt % conditioning ingredients such as quaternary ammonium compounds or amphoteric polymers, proteins, etc., and 1-40% surfactants. Hair conditioners may also contain volatile or nonvolatile silicones. Hair conditioners would generally contain from 0.1 to 4 wt % salicylic acid.

Toners typically contain about 0-85 wt % alcohol, 0.01-5 wt % surfactant, and 0.1-5 wt % humectants, 0.1-85% water.

The salicylic acid may also be used in ointments, gels, or solutions. Suitable ointments are hydrophilic ointments (USP) or petroleum.

The amount of salicylic acid present in the final product depends on the product. For example, skin exfoliation products can use as high as 10% salicylic acid, acne treatment products generally contain 0.5 to 2 wt % salicylic acid, dandruff and seborrheic dermatitis, and psoriasis treatment products generally contain 3 wt % salicylic acid, and wart treatments and skin tag removers generally contain up to 40 wt % salicylic acid, typically 5 wt % to 40 wt % or 17 wt % to 25 wt %.

Example 1

A 36% salicylic acid was blended with 54% cocamidopropyl dimethylamine and 10% PEG-450. The resulting concentrated gel was a yellow opaque semi-solid gel.

The concentrated gel was diluted to 2 wt % active salicylic acid in water and separately in ethanol. The resulting solutions were clear and colorless. No precipitate was formed either in water or in ethanol. The pH of the water solution was approximately 3.2.

Stability tests were then performed on the water solution. The concentrated gel and the diluted 2 wt % active salicylic acid solution were prepared and subjected to accelerated stability protocol which consisted of five freeze/thaw cycles and two weeks in a 50° C. oven. Under both of these conditions there were no significant changes to either sample. The samples that were frozen were obviously solid when removed from the freezer and the 50° C. samples were less viscous. In both cases, when the samples returned to room temperature, they were essentially identical to the control samples. There was no color or viscosity change and no precipitate was formed.

The gel was also diluted to 25 wt % active salicylic acid in water. The resulting solution was a slightly viscous, yellow, clear solution. No precipitate was formed. A physical accelerated stability test was run on this prototype consisting of samples be held at 50° C. for two weeks and another sample run through five freeze/thaw cycles. Under both of these conditions there were no physical changes to the product include pH, viscosity, color and appearance.

Example 2

A lotion was prepared with 5.5% of the gel of example 1 in 90.5% water with 4% Egel 305 [Polyacrylamide (&) C12-13 isoparaffin (&) Laureth-7]. The result was a white lotion that would be applicable for an anti-acne product. The lotion underwent the same accelerated stability testing as mentioned in example 1 (50° C. for 2 weeks and 5 freeze/thaw cycles); there were no significant physical changes to the product during the stability testing.

Example 3

An anti-dandruff shampoo was prepared containing 3 wt % salicylic acid.

| | An anti-dandruff | | Percent |
|---|---|---|---|
| | | Water | 35.67 |
| Active ingredient | | Cocamidopropyl Dimethylamine (&) Salicylic Acid | 8.33 |
| Surfactant blend | | PEG-80 Sorbitan Laurate (&) Cocamidopropyl Betaine (&) Sodium Trideceth Sulfate (&) Glycerin (&) Disodium Lauroamphodiacetate (&) PEG-150 Distearate (&) Sodium Laureth-13 Carboxylate | 50.00 |
| Thickener | | PEG-120 Methyl Glucose Trioleate (&) Propylene Glycol (&) Water (Glucamate ™ LT) | 5.00 |
| Preservative | | Propylene Glycol (&) Diazolidinyl Urea (&) Methylparaben (&) Propylparaben (Nipaguard PDU) | 1.00 |
| | | Citric Acid | qs to pH |
| | | | 100.00% |

In an appropriate container, water, and salicylic acid gel were mixed until uniform. Sulfochem B-NBB, Glucamate LT and Nipaguard PDU were added and mixed until homogenous. Then citric acid was added, with continued mixing, until the batch reached pH of approximately 4.0. Viscosity: >1300 cp. Stability: Passed 2 weeks 50° C.; 5 Freeze/Thaw cycles.

Example 4

A wart remover was prepared containing 17% salicylic acid.

| | | | Percent |
|---|---|---|---|
| | | Water | 41.8 |
| Active Ingredient | | Cocamidopropyl Dimethylamine (&) Salicylic Acid | 47.2 |
| | | Propanediol (Zemea®) | 5.0 |
| | | Hydrogenated Methyl Abeitate (Meristant ® 101L) | 1.0 |
| | | Alcohol | 4.0 |
| Preservative Blend | | Phenoxyethanol (&) Methylparaben (&) Ethylparaben Propylparaben (&) Isobutylparaben | 1.0 |
| | | Citric Acid | Qs |
| | | | 100.0% |

In an appropriate container, water and salicylic acid gel were blended until homogenous. In a separate container, alcohol and Meristant® 101 L were mixed until homogenous and then added to and mixed with the salicylic acid gel/Water blend. Zemea® and Phenonip were then added to the blend and mixed until clear. The pH was adjusted with citric acid to 4-4.5 as necessary.

Example 5

A 40% salicylic acid was blended with 60% cocamidopropyl dimethylamine and then combined in a 4:1 weight ratio with stearyl alcohol. The resulting blend was mixed and heated to 65-70° C. Mixing and heating were maintained until all of the stearyl alcohol had melted and the blend was clear. The heat was then turned off with continued mixing. The blend was mixed until the batch cooled to 20-25° C. The batch was then allowed to sit for a 3-4 hours. The resulting material was a solid. Viscosity measurements were difficult but all results were above 100,000 cps at 25° C.

Example 6

A 40% salicylic acid was blended with 60% cocamidopropyl dimethylamine and then combined in a 47:1 weight ratio of a high molecular weight hydroxypropyl cellulose (HPC). The resulting blend was then heated to 70-75° C. and mixed until the HPC has dispersed as evenly as possible. The mix time was between 2-3 hours. The heat was then removed from the blend which was mixed continuously until the blend reached room temperature. The resulting blend was a syrupy liquid with a viscosity greater than 100,000 cps at 25° C.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A composition in the form of a stable gel and containing, based on the total weight of the gel:
   a. salicylic acid which is normally soluble in water, but which is present in the gel in soluble form in an amount of at least 30 wt. %;
   b. a stabilize liquid nitrogen-containing compound that is an alkylamido amine which functions as a stabilizer (hereafter for convenience "stabilizer") and is present in an amount of at least 40 wt. %, wherein said stabilizer and the amount thereof function to form said stable gel by solubilizing and dissolving said salicylic acid; and
   c. at least one polyethylene glycol thickener in an amount of at least 1 wt. %.

2. The concentrated salicylic acid gel according to claim 1, wherein the polyethylene glycol thickener is present in an amount of at least 5 wt. %.

3. The concentrated salicylic acid gel according to claim 1, wherein the polyethylene glycol thickener is present in an amount of at least 20 wt. %.

4. The concentrated salicylic acid gel according to claim 1, wherein the polyethylene glycol thickener is present in an amount of at least 30 wt. %.

5. The concentrated salicylic acid gel according to claim 1, wherein the polyethylene glycol thickener is present in an amount of 20 wt. % to 50 wt. %.

6. The concentrated salicylic acid gel according to claim 1, wherein the polyethylene glycol thickener is present in an amount of up to 50 wt. %.

7. The concentrated salicylic acid gel according to claim 1 consisting of 30 to 60 wt. % salicylic acid, 40 to 70 wt. % stabilizer, and 1 to 20 wt. % polyethylene glycol thickener.

8. The concentrated salicylic acid gel according to claim 1 consisting of 35 to 55 wt. % salicylic acid, 45 to 60 wt. % stabilizer, and 5 to 20 wt. % polyethylene glycol thickener.

9. The concentrated salicylic acid gel according to claim 1, wherein the stabilizer is cocamidopropyl dimethylamine.

10. The concentrated salicylic acid gel according to claim 1 wherein the thickener is at least one selected from the group consisting of agar, algin pectin, bentonite, chitosan, cellulose, carrageenan, chitin, cassia gum, cetyl glycol, clay, croscarmellose, dextrin, xanthan gum, gelatin, hectorite, silica, hydroxyethylcellulose, hydroxypropylcellulose, methylcellulose, microcrystalline cellulose, pectin, polyester-5, polyether-1, polyglycerin-20, polyglycerin-40, sclerotium gum, sodium stearate, starch, beeswax, ceresin, an alcohol, or a polyethylene glycol.

11. The concentrated salicylic acid gel according to claim 1 wherein the polyethylene glycol thickener is selected from the group consisting of PEG-450, PEG-800, PEG-2M, PEG-SM, PEG-7M, PEG-9M, PEG-14M, PEG-20M, PEG-23M, PEG-25M, PEG-45M, PEG-65M, PEG-90M, PEG-115M, PEG-160M, and PEG-180M.

12. The composition according to claim 1 consisting of salicylic acid, cocamidopropl dimethylaminem, and at least one polyethylene glycol thickener is selected from the group consisting of PEG-450, PEG-800, PEG-2M, PEG-SM, PEG-7M, PEG-9M, PEG-14M, PEG-20M, PEG- 23M, PEG-25M, PEG-45M, PEG-65M, PEG-90M, PEG-115M, PEG-160M, and PEG- 180M.

* * * * *